(12) United States Patent
Russo et al.

(10) Patent No.: US 10,195,363 B2
(45) Date of Patent: Feb. 5, 2019

(54) SELECTABLE NEEDLE SYRINGE WITH RETRACTION PLUNGER

(71) Applicant: UNL Holdings LLC, New York, NY (US)

(72) Inventors: Robert Scott Russo, Gettysburg, PA (US); Daniel A. Heinsbergen, Narberth, PA (US)

(73) Assignee: UNL Holdings LLC, New York, NY (US)

( * ) Notice: Subject to any disclaimer, the term of this patent is extended or adjusted under 35 U.S.C. 154(b) by 108 days.

(21) Appl. No.: 15/115,898

(22) PCT Filed: Feb. 3, 2015

(86) PCT No.: PCT/US2015/014260
§ 371 (c)(1),
(2) Date: Aug. 1, 2016

(87) PCT Pub. No.: WO2015/117135
PCT Pub. Date: Aug. 6, 2015

(65) Prior Publication Data
US 2017/0165432 A1 Jun. 15, 2017

Related U.S. Application Data

(60) Provisional application No. 61/934,963, filed on Feb. 3, 2014.

(51) Int. Cl.
| | | |
|---|---|---|
| *A61M 31/00* | (2006.01) | |
| *A61M 5/32* | (2006.01) | |
| *A61M 5/315* | (2006.01) | |

(52) U.S. Cl.
CPC ...... *A61M 5/3234* (2013.01); *A61M 5/31501* (2013.01); *A61M 5/31511* (2013.01);
(Continued)

(58) Field of Classification Search
CPC ........ A61M 5/31511; A61M 2005/323; A61M 2005/3241; A61M 2205/273;
(Continued)

(56) References Cited

U.S. PATENT DOCUMENTS

| | | |
|---|---|---|
| 2011/0092902 A1 | 4/2011 | Kiehne |
| 2012/0022447 A1 | 1/2012 | Oliver et al. |

(Continued)

FOREIGN PATENT DOCUMENTS

| | | |
|---|---|---|
| EP | 1 232 763 A1 | 8/2002 |
| EP | 2 403 563 A1 | 1/2012 |

(Continued)

OTHER PUBLICATIONS

International Search Report and Written Opinion, dated May 14, 2015, issued in International Patent Application No. PCT/US2015/014260, filed Feb. 3, 2015.

(Continued)

*Primary Examiner* — Rebecca E Eisenberg
(74) *Attorney, Agent, or Firm* — Hamilton, Brook, Smith & Reynolds, P.C.

(57) ABSTRACT

The present embodiments provide for a syringe and a retraction plunger assembly configured to accept various retractable needle assemblies, which are capable of cooperating to provide a retraction safety syringe. In particular, the syringe includes a barrel and a retraction plunger assembly comprising a control unit attached to a plunger and releasably engaged to a housing, and at least one biasing means disposed within the plunger assembly. Upon completion of dose delivery via a retractable needle, the control unit disengages from housing and the biasing member retracts the plunger and a connected needle into the barrel. Various (Continued)

elements are configured to prevent further use of the syringe. The control unit can be used to control a rate of needle retraction.

25 Claims, 7 Drawing Sheets

(52) U.S. Cl.
CPC ..... *A61M 5/3221* (2013.01); *A61M 2005/323* (2013.01); *A61M 2005/3241* (2013.01); *A61M 2205/273* (2013.01); *A61M 2205/586* (2013.01)

(58) Field of Classification Search
CPC ............ A61M 5/31501; A61M 5/3221; A61M 5/322; A61M 5/3232; A61M 5/34
See application file for complete search history.

(56) References Cited

U.S. PATENT DOCUMENTS

| 2013/0102973 A1 | 4/2013 | Thorley et al. |
| 2013/0211338 A1 | 8/2013 | Roberts et al. |
| 2013/0310759 A1 | 11/2013 | Hourmand et al. |

FOREIGN PATENT DOCUMENTS

| WO | 2004/082747 A1 | 9/2004 |
| WO | 2006/108243 A2 | 10/2006 |
| WO | 2009/003234 A1 | 1/2009 |
| WO | 2010/100244 A1 | 9/2010 |

OTHER PUBLICATIONS

International Preliminary Report on Patentability dated Aug. 18, 2016 in International Application No. PCT/US2015/014260, filed Feb. 3, 2015.

SELECTABLE NEEDLE SYRINGE WITH RETRACTION PLUNGER

RELATED APPLICATIONS

This application is a 371 of International Patent Application Serial No. PCT/US2015/014260, filed on Feb. 3, 2015, which claims priority benefit of U.S. Provisional Application Ser. No. 61/934,963, filed on Feb. 3, 2014, both of which are incorporated fully herein for all purposes.

FIELD

The embodiments described herein relate to injection syringes. More specifically, the embodiments relate to retraction safety syringes having retraction plunger assemblies and configured to accept and retract a number of different retractable needle attachments.

BACKGROUND

Today's healthcare practitioners are usually provided with ready-to-use medical devices. This is particularly true of syringes that are used to administer parenteral drugs and other medical solutions, because these devices can be sterilized during production. A syringe typically includes a barrel that has a substantially closed distal end, and an opposite proximal open end that is sealed by a slidable piston plunger. The distal end of the syringe includes a dispensing port, typically communicating with a luer fitment, for dispensing the contents of the syringe. A removable end-cover, such as a luer cap, is placed over the luer fitment during manufacture to seal contents within the syringe barrel. The syringe may be prefilled with a liquid, part-filled with a solid or liquid, or empty. Prefilled syringes are advantageous in avoiding confusion regarding whether a vial is multi-dose or single-dose, or which diluent should be used with a given medicament; and prefilled syringes may provide a suitable means for storage and shipment of sensitive pharmaceuticals such as biologics. Additionally, use of prefilled syringes, particularly those with safety mechanisms, may limit a health professional's risk of inadvertent needle-stick injuries or possible exposure to infective pathogens or other contaminants associated with used syringes.

Further regarding pathogens and contaminants, the practice of sharing used needles or syringes between successive users can transfer pathogens such as Human Immunodeficiency Virus and Hepatitis Virus, with subsequent severe repercussions for the infected and high social cost in providing medical care for sufferers. In response to this practice, safety syringes have been developed that prevent re-use of a used syringe.

For example, one approach has been to develop safety syringes comprising a compressed spring mechanism that, following injection, permanently retracts the needle into the barrel of the syringe. Generally, spring decompression is relatively uncontrolled, and excessively forceful needle retraction can result in blood splattering when air is forced from the syringe barrel as the needle retracts into the barrel. Further, many such retraction syringes have highly specialized needle assemblies that stymy replacing a defective needle or selecting a desired needle size. An additional complication involves ensuring that the needle does not inadvertently retract into the syringe barrel, for example when piercing the skin before injection, while ensuring retraction after delivery of syringe contents. Mechanisms that achieve these functions may challenge designers, particularly if competing interests of manufacturing costs and reliability are balanced for a commercially viable retraction syringe. These problems are often more marked in the context of a retraction syringe having a replaceable needle assembly. Therefore, there is a need for more "user friendly" retractable syringes that do not compromise the safety features provided by the syringe.

SUMMARY

The embodiments described herein provide for syringes with retraction plunger assemblies, configured to accept various retractable needle assemblies and cooperate as a retraction safety syringe. The embodiments also relate broadly to improved needle retention or retraction mechanisms, comprising respective elements of a plunger capable of engaging and retracting a retractable needle. In particular, the present embodiments provide for safety retraction syringes that enable a controlled rate of needle retraction: the plunger, plunger seal, needle and other retractable components are capable of retracting at a rate controlled or controllable by the operator. Additionally, the safety syringes of the present embodiments can be prefilled in standard processing systems such as 'fill-finish' systems. The present embodiments also provide for devices that can accept or connect to a broad range of needle assemblies, or needle-less access devices ("NLADs"), such as intra-venous lines. Additionally, the present retraction plungers allow the selection of a needle from various needle assemblies, to provide substance delivery to a selected patient site, such as a subcutaneous or intramuscular site.

In one aspect the embodiments described herein provide for retraction plunger assemblies for use with a safety syringe comprising a retraction plunger assembly that includes a plunger connected at its proximal end to a control unit; a biasing member disposed at least partially within the plunger; and a housing detachably attached to the control unit; wherein the plunger, control unit, and housing are configured to cooperate in maintaining the biasing member in an energized state prior to plunger retraction. More specifically, the present embodiments provide for a plunger assembly comprising a plunger configured for positioning and axial displacement within a syringe barrel, the plunger having a proximal portion, a distal portion, and a cavity there between, and the distal portion of the plunger is fixed to a plunger seal that includes a coupling configured to couple to retractable needle portion of a retractable needle assembly. The plunger assembly includes a control unit fixed at the proximal portion of the plunger, wherein the control unit comprises at least one detachable attachment for detachably attaching to a housing. The plunger assembly includes a housing detachably attached to the control unit, wherein the housing comprises at least one permanent fastening configured to secure the housing to a fitting disposed at the proximal end of the syringe barrel. The plunger assembly also includes at least one biasing member disposed in an energized state within the plunger assembly, wherein the biasing member is positioned between the control unit and housing and at least partially within the plunger cavity, and wherein the control unit attachment to the housing maintains the biasing member in the energized state. In some embodiments, the housing of the retraction plunger assembly includes at least one retaining element configured to reversibly link at least one of the control unit, the plunger, or the biasing member. In some embodiments, the retraction plunger assembly includes at least one locking part configured to lock the plunger in a fixed position. This aspect further includes a syringe comprising the retraction plunger assembly, in which the syringe can further include a retractable needle assembly that comprises a proximal needle portion configured to couple to the plunger seal coupling. In some embodiments, the syringe further comprises an injectable substance, i.e., the syringe is prefilled.

Another aspect of the embodiments described herein provides for a safety syringe comprising a barrel having a proximal end and a distal end; the distal end of the barrel comprising a distal connector configured to engage a retractable needle assembly; a retraction plunger assembly comprising a plunger disposed in the proximal end of the barrel and configured for axial displacement within the barrel, the plunger having a proximal portion and a distal portion, a control unit fixed at the proximal portion of the plunger, a housing detachably attached to the control unit, and at least one biasing member disposed within the plunger assembly; and a release member disposed at the proximal end of the barrel and configured to detach the housing from the control unit upon full depression of the plunger into the barrel. The control unit may include at least one attachment for detachably attaching to the housing. The housing may include at least one fastener configured to secure the housing to a fitting disposed at the proximal end of the barrel. The housing may also include at least one retaining element configured to releasably link at least one of the control unit, the plunger, or the biasing member. This retaining element may also be configured to permanently secure the housing to a fitting disposed at the proximal end of the barrel. The release member may further include a fitting to permanently secure the housing. In some embodiments, the release member and the fitting are included in or on a collar affixed to the proximal end of the syringe barrel. The distal portion of the plunger may further comprise a plunger seal; and the plunger seal may further include a coupling configured to couple to a retractable needle portion of a retractable needle assembly. Alternatively, the distal portion of the plunger may include a coupling configured to couple to a retractable needle portion of a retractable needle assembly. In at least one embodiment, the biasing member is held in an energized state when the control unit is attached to the housing. Conversely, the biasing member is no longer held in an energized state when the control unit is detached from the housing. Upon full depression of the plunger into the barrel, the release member detaches the control unit attachment from the housing, allowing the biasing member to transform from an energized to a non-energized state. When the plunger has been coupled to a retractable needle, the transformation of the biasing member retracts both the plunger and the coupled retractable needle. The rate of retraction can be slowed by controlling the upraising the control unit. In at least one embodiment, the safety syringe of this aspect includes at least one locking part configured to lock the plunger in a fixed position following needle retraction.

A particular embodiment provides for a safety syringe comprising a barrel having a proximal end and a distal end, the distal end of the barrel having a distal connector configured to engage a retractable needle assembly; a retraction plunger assembly comprising a plunger disposed in the proximal end of the barrel and configured for axial displacement within the barrel, the plunger having a proximal portion and a distal portion, wherein the distal portion of the plunger is fixed to a plunger seal including a coupling configured to couple to a retractable needle portion of a retractable needle assembly, a control unit fixed at the proximal portion of the plunger, wherein the control unit comprises at least one detachable attachment for detachably attaching to a housing, a housing detachably attached to the control unit, wherein the housing comprises at least one permanent fastener configured to secure the housing to a fitting disposed at the proximal end of the barrel, and at least one retaining element configured to reversibly link at least one of control unit, plunger, or biasing member, and at least one biasing member disposed in an energized state within the plunger assembly; and a collar affixed to the proximal end of the syringe barrel, the collar comprising a release member configured to detach the control unit attachment from the housing upon full depression of the plunger into the barrel, and a fitting to permanently secure the housing fastener to the proximal end of the barrel. Upon full depression of the plunger into the barrel, the permanent fastener of the housing secures the housing to the collar fitting, and the release member detaches the control unit attachment from the housing, releasing the biasing member from the energized state so that it expands within the plunger, and thereby draws the plunger proximally through the housing to retract the plunger; wherein the rate of retraction can be adjusted by controlling the upraising of the control unit. Additionally, the retaining element of the housing can be configured to lock the housing to a fitting disposed at the proximal end of the barrel. The syringe of this embodiment can also include at least one locking part that locks the plunger in a fixed position following retraction.

Another aspect of the present embodiments relates to kits comprising the retraction plunger assembly as described herein. Such kits may further comprise at least one retractable needle assembly having a retractable needle portion configured to couple to the plunger of the retraction plunger assembly. For example, a retraction syringe kit can include a plurality of needle assemblies including a 0.5 inch needle, a 1.0 inch needle, and a 1.5 inch needle, though a range of needle lengths and gauges may be utilized and incorporated within the needle assemblies and kits of the present embodiments.

Another aspect of the present embodiments provides for methods of using a retraction safety syringe, comprising the steps of, for example, obtaining a retraction safety syringe comprising the retraction plunger assembly as described herein, wherein the syringe is fillable or prefilled with a substance; selecting a retractable needle assembly having a retractable needle portion configured to couple to the plunger; and attaching the selected retractable needle assembly to the retraction safety syringe. Additionally, the method can include depressing the control unit to expel the substance and couple the plunger to the retractable needle portion, secure the permanent fastener of the housing to a fitting disposed at the proximal end of the syringe barrel, and detach the control unit from the housing, thereby releasing the biasing member from the energized state; and upraising or retracting the control unit at a controlled rate to retract the needle into the syringe.

BRIEF DESCRIPTION OF THE DRAWINGS

Some non-limiting embodiments are described with reference to the drawings.

FIG. 5A shows a cross sectional view of the proximal portion of the plunger and the control unit engaged with the housing; FIG. 5B is an isometric cross sectional perspective of the control unit engaged with the housing; FIG. 5C is a 90° rotated cross sectional perspective view of the proximal end of the plunger and the control unit, engaged with the housing; FIG. 5D is a perspective view similar to FIG. 5C (rotated 90° from FIG. 5A and adjusted for perspective), excluding the plunger and showing the control unit engaged with the housing; the arrows indicate the direction in which the control unit attachment is deformed to detach the control unit from the housing.

FIGS. 6A and 6B are isometric perspectives; FIG. 6C shows both perspective and cross-sectional views, and FIG. 6D is a cross sectional view.

DETAILED DESCRIPTION

Figure 1A:
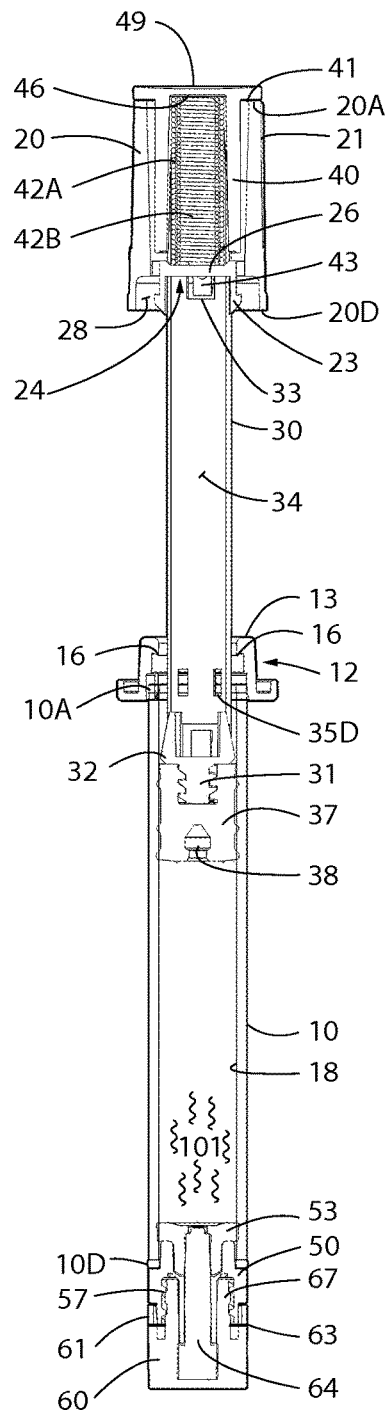
FIG. 1A and FIG. 1B show 90° rotated cross sectional views of an embodiment of a prefilled syringe having a retraction plunger assembly compatible with selectable retractable needle assemblies.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the applicants are not entitled to antedate such disclosure by virtue of prior invention or for any other reason. All statements as to the date or representation as to the contents of these documents are based on the information available to the applicants and does not constitute any admission as to the correctness of the dates or contents of these documents.

As used herein and in the claims, the singular forms include the plural reference and vice versa unless clearly indicated otherwise by context. The term "or" is inclusive unless modified, for example, by "either." Throughout this specification, unless otherwise indicated, "comprise," "comprises" and "comprising" are used inclusively rather than exclusively, so that a stated integer or group of integers may include one or more other non-stated integers or groups of integers. Other than in the operating examples, or where otherwise indicated, all numbers expressing quantities of ingredients or reaction conditions used herein should be understood as modified in all instances by the term "about."

Unless otherwise defined, scientific and technical terms used in connection with the formulations described herein shall have the meanings that are commonly understood by those of ordinary skill in the art. The terminology used herein is for the purpose of describing particular embodiments only, and is not intended to limit the scope of the present invention, which is defined solely by the claims. The terms male and female may be used interchangeably to describe corresponding components or complementary aspects thereof and are not a limitation to either particular structure unless context clearly indicates otherwise.

As used herein to describe the relative positions of the components of the present embodiments, the terms "axial" or "axially" refer generally to a longitudinal axis "A" of the barrel of a syringe and plunger in which or around components are positioned, although not necessarily symmetrically there-around. The term "radial" refers generally to a direction perpendicular to axis A. The terms "proximal," "rear," "rearward," "back," or "backward" refer generally to an axial direction in the direction "P." The terms "distal," "front," "frontward," "depressed," or "forward" refer generally to an axial direction in the direction "D," toward the dispensing end of the syringe.

"Fluid" refers primarily to liquids, but can also include suspensions of solids dispersed in liquids (dispersions, suspensions, colloidal mixtures), emulsions, liposomal compositions, and gasses dissolved in or otherwise present together within liquids inside the fluid-containing portions of syringes. "Fluid" may include agents, drugs, pharmaceuticals, and the like, but is not limited to such active agents.

As used herein, the term "glass" should be understood to include other similarly non-reactive materials suitable for use in a pharmaceutical grade application that would normally require glass (e.g., Type I borosilicate glass), including but not limited to certain non-reactive polymers such as cyclic olefin copolymers (COC) and cyclic olefin polymers (COP).

The term "plastic" may include both thermoplastic and thermosetting polymers. Thermoplastic polymers can be re-softened to their original condition by heat; thermosetting polymers cannot. As used herein, the term "plastic" refers primarily to moldable thermoplastic polymers such as, for example, polyethylene and polypropylene, or an acrylic resin, that also typically contain other ingredients such as curatives, fillers, reinforcing agents, colorants, or plasticizers, etc., and that can be formed or molded under heat and pressure. As used herein, the term "plastic" can include pharmaceutical grade non-reactive polymers or elastomers that are approved for use in applications where they are in direct contact with therapeutic substances, such that the plastics do not interact with the substances contacting the plastic and are not readily susceptible to leaching or gas migration under ambient temperature and pressure.

The term "elastomer," "elastomeric" or "elastomeric material" refers primarily to cross-linked thermosetting rubbery polymers that are more easily deformable than resilient plastics, are approved for use with pharmaceutical grade substances, and are not readily susceptible to leaching or gas migration under ambient temperature and pressure. It is appreciated in the art that particular elastomeric polymers are better suited for contact with pharmaceuticals than are some particular plastics, hence the elastomeric material can be a biocompatible material. As used herein, the term "elastomer," "elastomeric" or "elastomeric material" may also include other biocompatible materials, such as styrenic block copolymers (TPE-s), polyolefin blends (TPE-o), elastomeric alloys (TPE-v or TPV), thermoplastic polyurethanes (TPU), thermoplastic copolyesters, or thermoplastic polyamides, among other biocompatible materials which are approved for use with pharmaceutical grade substances, and are not readily susceptible to leaching or gas migration under ambient temperature and pressure.

According to various aspects and embodiments described herein, reference is made to a "biasing member" or "biasing means", which may be any member, device or mechanism that is capable of storing and releasing energy. Non-limiting examples include springs, such as for example a coiled spring, a compression or extension spring, a torsional spring, and a leaf spring, a resiliently compressible or elastic band, or any other member with similar functions. In at least one embodiment of the present invention, the biasing member is a spring, such as a compression spring. In at least one other embodiment, the biasing member consists of two springs, which can be arranged in coaxial concentric fashion within the retraction plunger assembly.

References to "prefillable" generally refer to syringes comprising components for filling with a substance prior to dispensing the substance for its intended use. More specifically, in the context of the syringe embodiments, the term "prefillable" refers to a configuration or state in which a substance may be introduced into the syringe any time prior to the dispensing by the syringe of the substance(s) for their intended use (such as delivery into a subject or device either directly or indirectly). A prefillable syringe thus includes syringes described herein as prefilled, fill-at-time-of-use, fill-on-demand, ready-to-use, and the like.

References to "pharmaceutical agent," "pharmaceutically active," "pharmaceutical," "drug," "medicament" "active agent," "active drug" and the like, refer in a general sense to substances useful in the medical and scientific arts as suitable for delivery via a syringe, including, for example, drugs, biologics, diagnostic agents (e.g, dyes or contrast agents) or other substances used for therapeutic, diagnostic, or preventative (e.g., vaccines), or research purposes. Example pharmaceutical agents include biologics, vaccines, chemotherapeutic agents, contrast agents, small molecules, immunogens, antigens, interferons, polyclonal antibody preparations, monoclonal antibodies, anesthetics, interfering RNAs, gene vectors, insulins, or combinations of any of these. "Inactive" substances refer to carriers, excipients, diluents, and the like, which are well-known in the art, although such substances may have beneficial function in the mixed injectable, such as, for example, adjuvants, isotonic or buffering agents. These active or inactive substances may also include substances having immediate, delayed or sustained release characteristics.

Existing commercial syringes with needle safety mechanisms include relatively complicated component assemblies that add substantially to the complexity and cost of manufacture. Additionally, existing configurations may not adequately address challenges related to patient and operator safety, ease-of-operation, and drug filler or pharmaceutical company manufacturing systems, among other challenges. The embodiments described herein address these challenges, and others, without comprising the manufacturability, stability, and durability of the described devices.

The embodiments described herein provide for retraction plunger assemblies for use in safety syringes, having improved needle retention or retraction mechanisms, comprising respective elements of a plunger capable of engaging and retracting various retractable needle assemblies. In particular, the present embodiments provide for retraction plunger assemblies that enable a controlled rate of needle retraction: the plunger, plunger seal, needle, and other components are capable of retracting at a rate controlled or controllable by the operator. Additionally, the safety syringes comprising the retraction plunger assemblies of the present embodiments can be prefilled in standard processing systems such as 'fill-finish' systems. The present embodiments also provide for devices that can accept or connect to a broad range of needle assemblies, or needle-less access devices ("NLADs"), such as intra-venous lines. The present embodiments, having retraction plungers and facilitating selection from various retractable needle assemblies, can provide substance delivery to various patient sites, such as subcutaneous or intramuscular sites.

More specifically, at least one embodiment described herein provides for a retraction plunger assembly that includes a plunger connected at its proximal end, permanently or temporarily, to a control unit; a biasing member disposed at least partially within the plunger; and a housing detachably attached to the control unit; wherein the plunger, control unit, and housing are configured to cooperate in maintaining the biasing member in an energized state prior to plunger retraction. In at least one embodiment, a syringe comprising the retractable plunger assembly further comprises a collar affixed to the proximal end of the syringe barrel. The collar may include a release member that facilitates detachment of the control unit and the plunger housing. The collar may also include a fitting that permanently secures a fastener of the housing. Alternatively, the release member or fitting can be configured apart from the collar. The plunger also comprises, at its distal end, a plunger seal and a needle-engaging coupler configured to couple a needle body or other linkage of a retractable needle assembly, to facilitate retraction of the retractable needle. The needle engaging coupler of the plunger may be part of the plunger seal.

In at least one embodiment, the plunger assembly is configured so that at full depression of the plunger (i.e., end-of-dose), a release member disposed at the proximal end of the syringe barrel causes the attachment of the plunger control unit to detach from the housing, which activates release of the biasing member. Upon this release, the housing is maintained in position on the syringe barrel, for example by a fastening and corresponding a fitting on or in the collar or other aspect on or in the barrel, while the plunger is driven in the proximal direction by the released biasing member (i.e., retracted). Such activation and release of the biasing member occurs after the retractable needle has coupled to the plunger (or a component thereof), so that the plunger, plunger seal, and needle are moved jointly in the proximal direction for needle retraction into the syringe barrel. Importantly, the operator can upraise the control unit, particularly using an interface on the proximal surface of the control unit, to control the retraction of the needle.

A portion of the plunger, such as the proximal portion, may be referred to or equivalent to a control rod. The plunger may be affixed to the control unit, or be contiguous single unit piece comprising both the plunger and the control unit. In at least one embodiment, the biasing member resides and functions at least partially within a cavity (or void) in the plunger. For example, the plunger may be configured such that the biasing member resides partially within the plunger and is held in an energized state by an attachment of the control unit detachably attached to the housing. In at least one embodiment, the plunger length comprises dual longitudinal slats (with corresponding dual openings), which allows limited proximal movement of the plunger through two complementary openings in the housing, as described further herein. In some embodiments, the plunger includes a means for irreversibly indicating the tampering with, or use of, the plunger. In other embodiments, the plunger includes at least one locking part that impedes motion of the plunger. For example, a locking part, after release of the biasing member, prevents the plunger from being re-deployed into the syringe barrel, or prevents the plunger from being pulled out of the syringe barrel.

As noted, the plunger typically includes a plunger seal, which can be mounted on or affixed to the plunger. The plunger seal can include a portion configured to engage a retractable needle (a retractable needle-engaging portion). The plunger seal is typically a partially or fully an elastomeric material that is, at least on the distal surface thereof, compatible with the intended contents of the syringe.

Suitably, the biasing member is any device or mechanism that can store energy in a releasable form, such as a spring (e.g., compression spring, coil spring, leaf spring, etc.), elastic, or the like. Biasing means can be used singly or in multiple. For example, two or more springs can be used in parallel, and have variable pitch or variable diameter for sufficient energy to provide efficient retraction, but not so much energy that premature release becomes likely or that controlled retraction rate is not maintained. In a particular embodiment, the biasing means is a spring, such as a coil spring. In another particular embodiment, the plunger assembly includes two compression coil springs arranged coaxially and concentrically within the plunger assembly. In at least one embodiment, the plunger assembly comprises a plunger, a control unit, a biasing member, and a housing, in which the plunger, control unit, and housing cooperate to releasably maintain the biasing member in an initially energized state.

In at least one embodiment, the housing of the plunger assembly comprises a portion configured to seat the distal end of a biasing member, which portion may be referred to as a floor or beam. The housing also includes at least one fastening for securing the housing to a fitting on or in the barrel, e.g., at the collar, to maintain the housing in fixed position and facilitate proximal-only movement of the biasing member and retraction of the plunger and needle assembly. The housing can also include at least one retaining element configured to releasably link the control unit or plunger. In a particular embodiment, the retaining element links both the control unit and the plunger, and can also be configured to engage the biasing member, by protruding inwards through openings aligned in the control unit and plunger. The retaining element engaged with the control unit and plunger is caused to be disengaged at end-of-dose, for example by downward pressure exerted against the collar or other release structure as the plunger is moved into the fully distal position by the operator, or by energy released from the biasing member upon detachment of the control unit and housing. Additionally, the housing can include at least one retaining element, which before release of the biasing member functions to stabilize the housing, control unit and plunger such that the biasing member is secured in the energized state prior to activation. The housing further includes slots, channels or openings configured to allow proximal passage of the plunger as it retracts after activation. For example, the housing can include two openings in the distal portion that allows proximal passage of a split plunger lengths therethrough. The housing may further include lock part or docks for securing the retracted plunger in place. The housing may also include exterior texture, grooves, handles or other features that may enhance operator grip on the proximal end of the safety syringe.

Alternatively, in some embodiments the control unit is releasably coupled to the plunger to maintain the biasing means in an energized state. In a particular form, the control unit is frangibly connected to the plunger. The control unit disengages from the plunger at end-of-dose to allow release of the biasing member and retraction of the needle assembly; in these embodiments the housing is optional.

In at least one embodiment, the retraction syringe may further comprise one or more locking systems or mechanisms that minimize possible re-use of the syringe or prevent withdrawal of the needle assembly from the proximal end of the barrel once the needle has been retracted. The retraction plunger assembly may further include at least one locking mechanism that prevents the needle from being redeployed following retraction. These mechanisms are generally configured to maintain the plunger in the retracted position following retraction of the needle. In some embodiments, the plunger housing comprises one or more lock elements capable of forming a locking system with the barrel, or a collar mounted to the barrel. In some embodiments, the plunger comprises one or locking elements capable of forming a locking system with the barrel or a collar mounted to the barrel, or with the housing. In some embodiments, the barrel or a collar mounted to the barrel comprises one or more lock parts or fittings capable of forming a locking system with the plunger or the housing.

Additionally, the syringe components can be configured with features that prevent inadvertent pushing or pulling of the plunger before or during various stages of device operation. For example, tabs or outwardly projecting ridges on the plunger can cause resistance against the collar; windows or indentations in the plunger body can cause resistance when meeting inwardly projecting structures on the collar or housing; or androgynous units can cause resistance against each other. The plunger or collar may further comprise thread pieces or other devices that must be released or otherwise positioned before initiating injection, for example, to avoid inadvertent discharge from prefilled syringes.

In another aspect, the embodiments provide a needle assembly for a retraction syringe comprising a plunger and a barrel having a mounting member, in which the needle assembly comprises a needle that is engageable by the retraction plunger; a needle mount configured to connect with a distal connector or other mounting member of the barrel; and optionally a locking feature configured to engage the retractable needle and thereby prevent inadvertent proximal movement (i.e., retraction) of the retractable needle. In one embodiment, the needle assembly is a replaceable needle assembly, in which the needle assembly (and needle mount) is removably mountable to the mounting member. Typically, the mounting member and the needle mount comprise complementary mating members, although androgynous interfaces can be designed. A variety of retractable needle assemblies are compatible with the devices described herein, such as, for example, needle assemblies described in U.S. Pat. No. 8,167,837. See also U.S. Pat. Nos. 8,361,035 and 8,702,653; WO 2014/165205; WO 2014/197602; WO 2014/160864; WO 2013/126118; WO 2011/075760; WO 2009/003234; WO 2006/119570; WO 2006/108243.

In at least one embodiment, the mounting member further comprises a male fitment which is receivable by a female fitment of the needle mount (or vice versa). For example, the mounting member may comprise a screw-thread that, in use, is receivable by a complementary screw thread of the needle mount (or vice versa). In a particular embodiment, the mounting member may utilize a screw-thread and a male fitment to be received by a corresponding screw-thread and female fitment of the needle mount. This configuration may be similar to that known as a luer connection or, more specifically, a luer lock connection.

In at least one embodiment, the safety syringe further includes a distal connector that comprises a distal portion configured to engage a luer fitment, a proximal syringe barrel-engaging portion comprising an axial ledge configured to abut an axial distal edge of a glass syringe barrel, and a fluid aperture axially therethrough. Examples of some distal connector embodiments are described in further detail in PCT US2014/049962 and PCT US2014/050116.

The distal connector can further include a needle seal, located proximal to the connector, having a fluid aperture therethrough, wherein the needle seal fluid aperture is configured to align with the connector fluid aperture to form a fluid passage. In at least one embodiment, the distal connector (e.g., a luer connection adapter) also includes the needle seal that may be mounted within the barrel, for example, adjacent and proximal to the barrel-engaging portion of the connector, and further includes an aperture positioned to communicate with the connector. In a particular embodiment, the needle seal is engaged with a portion of the distal connector. Typically, the needle seal comprises an elastomeric polymer compatible with the intended contents of the syringe. In use, the needle seal may be compressible but substantially immobile. In at least one embodiment, the distal connector includes a tip cap having a body comprising a projection configured to engage the distal end of the connector fluid aperture and block fluid passage; which projection is constructed of an elastomeric or biocompatible material. Suitably, when the distal connector is coupled with a needle assembly, the cannula of the needle assembly is received or accommodated by, or extends through, the needle aperture of the connector. The distal connector can be configured to couple or mount to, or engage with, a needle assembly. The distal connector further comprises an aperture disposed centrally and axial within the connector, that may serve as a needle aperture. In some embodiments, the syringe barrel comprising the retraction plunger and distal connector further includes an assembly for retractable needle syringes.

At least one embodiment provides for syringe assembly comprising a retraction plunger assembly disposed at the proximal end of a glass barrel; and a distal connector comprising a distal portion configured to engage a luer fitment, a proximal syringe barrel-engaging portion with an axial ledge configured to abut the axial distal edge of the glass barrel, and a fluid aperture therethrough; wherein the syringe barrel is configured to include or receive a retractable needle assembly. In some embodiments, the distal connector includes a locking feature that permanently secures the distal connector to a connection such as a needle assembly. In some embodiments, the connector can connect with a distal tip cap, and the tip cap may include a means for irreversibly indicating the tampering with, or removal of, the tip cap, as described further herein. Some embodiments of the safety retraction syringe further include a tip cap having a body comprising a projection configured to engage the distal end of the connector fluid aperture and block fluid passage. In some embodiments, the tip cap includes a means for irreversibly indicating the tampering with, or use of, a needle assembly.

As noted, a releasing member (or release ring), which may be part of a collar, may be molded or attached (such as by glue) to the proximal end of the barrel to interact with the plunger assembly for retraction activation. Substantially at the same time as delivery of the syringe is completed and the plunger has travelled fully in the distal direction, and upon coupling of the plunger seal (or plunger distal sub-assembly) to the needle or needle-over-mold of the needle assembly, the control unit attachment is caused to contact the releasing ring. This causes the control unit to release from the housing (e.g., by deforming the control unit attachment from the interior ledge of the housing), thereby permitting at least one energized biasing member, held in the plunger between the control unit and the housing, to release energy. The housing is secured to the releasing ring or collar thereof (e.g., by the housing fastening securing a fitting in the collar) while the plunger is caused to retract in the proximal direction. Because the plunger seal and needle have coupled, they are caused to retract in the proximal direction, thereby pulling the entire needle into the barrel or barrel tip and preventing exposure of the needle to the operator or the patient. The rate of retraction of these components may be controlled by the operator by reducing distal pressure on the control unit or control rod portion of the plunger assembly. As the plunger reaches substantially complete retraction, lock parts (e.g., flexed plunger lock-out arms) prevent depression of the plunger inner in the distal direction, thereby disabling the used syringe.

Thus, an aspect of the present embodiments provides for safety syringes comprising a retraction plunger needle retraction mechanism, in which the syringe is prefilled or prefillable with a substance. The substance can be a pharmaceutical agent. As noted, pharmaceutical agents include, in a general sense, substances useful in the medical and scientific arts as suitable for delivery via a syringe, including, for example, drugs, biologics, diagnostic agents (e.g, dyes or contrast agents) or other substances used for therapeutic, diagnostic, or preventative (e.g., vaccines), or research purposes. For example, the pharmaceutical agent can be a biologic, a vaccine, a chemotherapeutic agent, a contrast agent, a small molecule, an immunogen, an antigen, an interferon, a polyclonal antibody preparation, a monoclonal antibody, an anesthetic, an interfering RNA, a gene vector, an insulin, or a combination of any of these. Substances that are inactive, but still relevant to medical and scientific arts as suitable for delivery via a syringe, include carriers, excipients, diluents, and the like; as well as substances having beneficial function, such as, for example, adjuvants, isotonic or buffering agents. These active or inactive substances may also include substances having immediate, delayed or sustained release characteristics. Such prefilled devices are exemplified in U.S. Pat. No. 8,167,837; further prefilled and prefillable devices are exemplified in WO 2015/009866, WO 2015/009871, and WO/2015/009868.

Another aspect of the present embodiments provides for prefilled syringes comprising a connector and retractable needle assembly, in which the syringe is prefilled or prefillable with a substance. The substance can be a pharmaceutical agent, such as, for example, Aciclovir, Amikacin, Amiodarone, Amoxicillin clavulanic acid, Atracurium besylate, Atropine, Azithromycin, Benzatropine mesylate, Bupivacaine, Butorphanol tartrate, Calcium Folinate, Carboplatin, Cefazolin, Cefepime, Cefotaxime Sodium, Cefoxitin sodium, Ceftriaxone sodium, Cefuroxime sodium, Chlorphenamine Maleate, Ciprofloxacin, Clindamycin phosphate, Deferoxamine Mesylate, Dexamethasone Sodium Phosphate, Diazepam, Diclofenac Sodium, Enalaprilat, Epinephrine, Epirubicin HCl, Esmolol, Fluconazole, Flumazenil, Fosphenytoin Sodium, Furosemide, Gemcitabine, Gentamicin sulphate, Granisetron, Hydrocortisone Hemisuccinate, Hyoscine Butylbromide, Irinotecan, Ketamine, Lidocaine Hydrochloride, Lincomycin, Methohexital Sodium, Methylprednisolone, Metoclopramide Hydrochloride, Metoprolol tartrate, Midazolam HCl, Milrinone, Naloxone HCl, Ondansetron, Pamidronic acid, Pancuronium Bromide, Paracetamol, Phenytoin, Piroxicam, Progesterone, Promethazine, Propranolol, Ranitidine, Sodium Valproate, Somatostatin, Teicoplanin, Terbutaline Sulfate, Tramadol Hydrochloride, Vancomycin Hydrochloride, Vecuronium Bromide, Vinorelbine, Water for Injection, Zoledronic Acid, or a mixture of any of these, optionally including additional pharmaceutically acceptable excipients as known in the art.

The embodiments of the present invention may further utilize additional components to enhance the use of the syringe, such as tamper-resistant or tamper-evident aspects to prevent or evidence tampering with the syringe. These tamper-resistant or tamper-evident aspects may deter or prevent an unauthorized user from, for example, removing the plunger rod, or tip cap, or provide evidence of tampering such that an unauthorized user will be discouraged from compromising the syringe. These tamper-resistance aspects could be located along the plunger, control unit, housing, collar, distal connector, tip cap, or needle cap. These tamper-resistance aspects could be axially positioned or longitudinally oriented, or in a number of other known configurations. The tamper-resistance aspects may additionally or alternatively be located on the plunger rod. Alternative mechanisms can be adapted for use with the connectors in relation to tamper-resistant devices; these mechanisms may be identical or similar to tamper-resistant devices described herein, but in certain embodiments may lack the biofeedback (tactile) associated with breaking of tamper-resistant or tamper-evident seals.

Figure 1B:
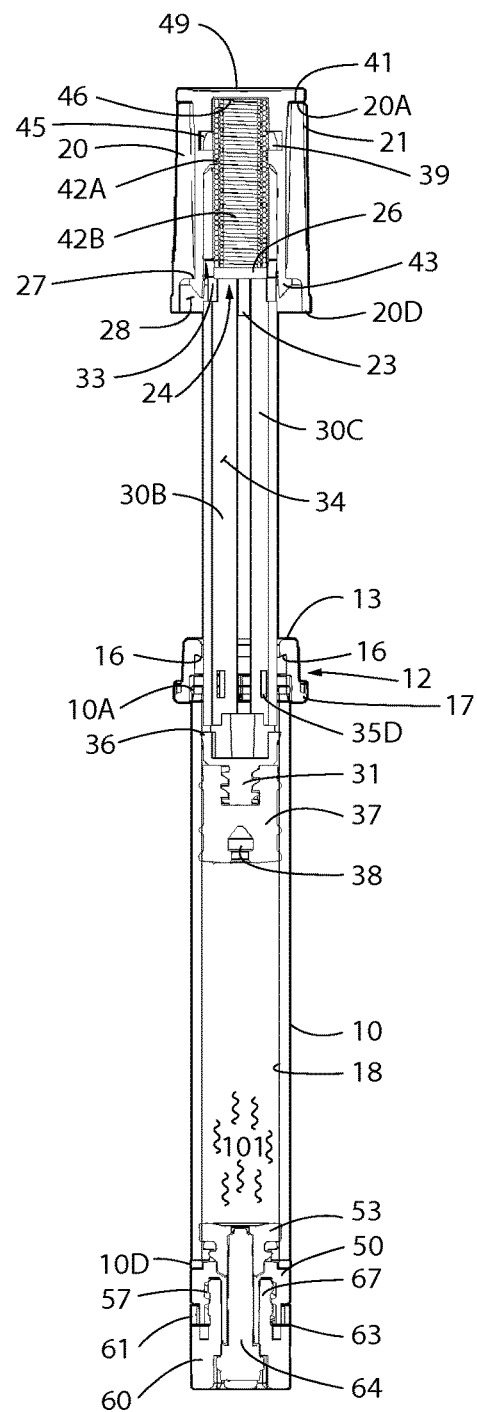

Referring to FIG. 1A and FIG. 1B, an embodiment of a retraction syringe comprises barrel 10 having proximal, plunger end 10A and a distal, connecting end 10D. Barrel 10 is substantially cylindrical in shape and is can be formed of glass, plastic, or any suitable material. This retraction syringe includes plunger 30 (sometimes called plunger inner) comprising plunger seal 37 mounted thereto. Barrel 10 further comprises inside wall 18 which together with needle seal 53 and plunger seal 37 define chamber space 101 in which fluid may be at least partially filled or prefilled. At the barrel's proximal end 10A is located collar 12, which may be mounted, glued, fitted or integrally formed with barrel 10. In embodiments in which barrel 10 is formed of glass, collar 12 is glued or otherwise adhered to barrel. In alternative embodiments in which barrel 10 is formed of plastic or other material, collar 12 can be formed integrally with barrel (e.g., by molding).

Further regarding an embodiment of a retraction plunger assembly, as shown in FIG. 1A and FIG. 1B, the plunger assembly includes plunger 30, joined to control unit 40 (sometimes plunger and control unit may be called control rod) within housing 20 (sometimes called plunger outer). Plunger 30 defines a void, cavity, or retraction path 34, and is partially discontinuous along the longitudinal axis, having sections 30B and 30C (see FIG. 1B). The proximal end of each plunger section 30B and 30C includes a projection 39, aligned and engaged with control unit window 45, securing and aligning plunger 30 in control unit 40 (see also FIG. 5A-FIG. 5D). The plunger can be joined to the control unit by complementary locking structures, or affixed by glue, or be joined to the control unit by any suitable means. In alternative embodiments, plunger 30 and control unit 40 or other control mechanisms can be formed (e.g., molded) as a single piece (e.g., forming a control rod).

Control unit 40 includes operator interface 49, which can be used to control both depression of the plunger assembly and upraising of the plunger (and retraction of a retractable needle), typically by interfacing with the operator's thumb or digit. Control aspects of control unit 40 also include detachable attachment 43 (sometimes called inner arms), which in this embodiment are extensions that detachably attach control unit 40 to housing 20 by attaching within the distal interior 28 at ledge 27 (sometimes called interior ledge) of housing 20 (see also FIG. 5A-FIG. 5D). The upper interior surface 46 of control unit 40 (surface opposite the interface 49 surface), and the interior surface 26 (sometimes called beam or platform) of the housing 20 form a "ceiling" 46 and a "floor" 26, respectively, that combine with interior space 44 of control unit 40 and interior space 34 of plunger rod 30 to form a cavity (see also FIG. 5A-FIG. 5D) that holds biasing members 42A and 42B. In this embodiment, biasing member 42A is a first, outer spring that surrounds a second, inner spring 42B. In FIG. 1A to FIG. 3B, the biasing members are held in the energized state by the structures just discussed.

In this embodiment, the exterior surface of housing 20 further comprises indentations or grooves 21, which provide grip or handling surfaces for the operator. Housing 20 further comprises retaining element 22, interior-facing tab or ridged structure that passes through control unit receiving opening 48 and plunger proximal window 35A (see also FIG. 5A-FIG. 5D), and functions to stabilize the plunger/housing interface and retain biasing members 42A and 42B in energized (compressed) state. Retaining element 22 may also impinge against or partially into biasing member 42A. In this way, retaining member(s) assist in impeding premature activation of the plunger retraction. Housing 20 also includes permanent fastener 23 configured to permanently secure a fitting at the proximal end of the barrel 10A as described further herein.

As noted, in this embodiment plunger 30 is not contiguous, and is partially divided along its length into two portions, 30B and 30C that allows plunger 30 to pass through slots 24 in housing 20 during needle retraction (see also FIG. 5A-FIG. 5D). The distal end of plunger, within barrel 10, includes two outwardly directed flared regions 32 on opposing sides of plunger 30; and two lock parts 36, which flex outwardly so that the plunger cannot be withdrawn from syringe barrel 10 because the flange 32 and locking tabs 36 extend beyond the circumference of opening 14 or catch against fitting 16 in collar 12. Plunger 30 is connected, at the distal end, to plunger seal 37 by complementary screw-threads 31; although the plunger can be connected to the plunger seal by any suitable means. Plunger seal 37 further includes a distal needle coupling aspect 38, configured as a recess to receive and thereby couple (engage) onto protrusion 72 on the proximal end of a selectable retractable needle assembly (see FIG. 4A and FIG. 4B). Although in this embodiment the coupling is achieved with a plunger "female" recess 38 and needle assembly "male" protrusion 72, respectively, the coupling engagement can be effected using any suitable type of coupling, complementary fitment or linkage arrangement, including androgynous interfaces.

At the barrel's distal connection end 10D is mounted distal connector 50 (e.g., a luer connection adapter). As shown in FIG. 1A and FIG. 1B, a selectable, retractable needle assembly has not yet been inserted into connector 50. Instead, tip cap 60 protects the sterility and integrity of the syringe. In particular, a stem 64 extends from the base of cap 60 through the aperture in connector 50 and needle seal 53. An elastomeric tip cap, for example, may be used for this purpose, although plastic tip caps and tip caps comprising other materials and combinations thereof may be used. It may be advantageous that stem 64 comprises or consists of an elastomeric material that is compatible with the contents intended for compartment 101. If the syringe is to be provided with a selected needle assembly, a needle assembly may be contained in a needle cap, as is known in the art. See, e.g., U.S. Pat. No. 8,167,837; PCT US2014/049962; PCT US2014/050116.

In the embodiment shown in FIG. 1A and FIG. 1B, distal connector 50 includes a feature for indicating the tampering with, or use of, the connector. More specifically, connector 50 is fitted with tamper-evident tip cap 60. Tip cap 60 includes a proximal portion 61 configured to link irreversibly to connector 50. Portion 61 is located proximally to scored line 63, which scored line 63 extends circumferentially around and partially, but not fully, through tip cap 60. Attempting to remove tip cap 60 from distal connector 50 provides biofeedback in the form of tangible resistance in attempting to remove the cap, a feeling of quick release when score line 63 is broken fully, and a slight noise like a snap or pop when score line 63 breaks and separates proximal portion 61 from the remainder of the tip cap structure. Therefore, if an operator sees that score line 63 is broken, or finds that tip cap 60 is removed easily without resistance or noise, then the operator can assume that the tip cap has been breached, and the device should not be used without consideration that the syringe contents may have been contaminated.

Figure 2A:
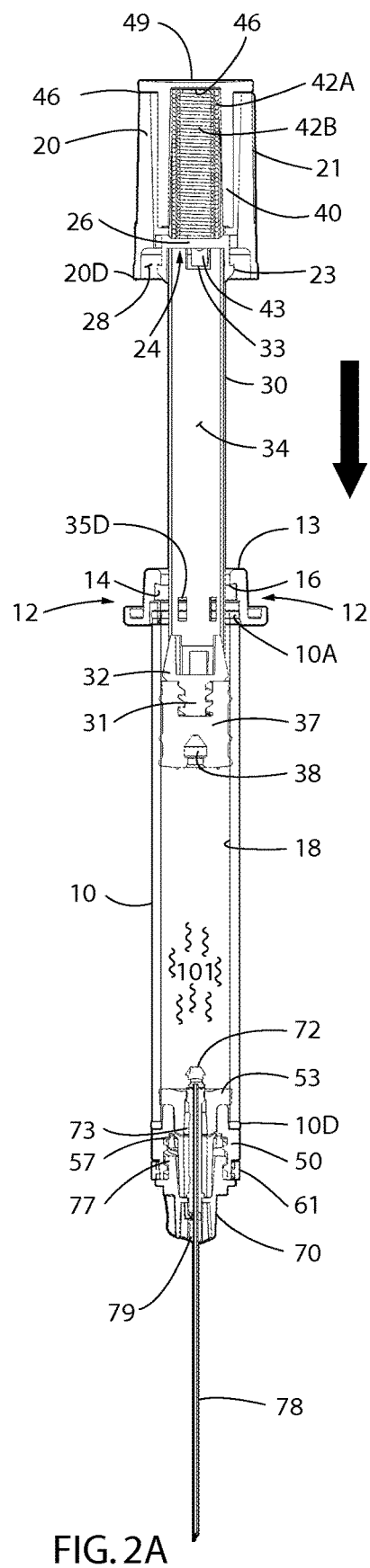
FIG. 2A and FIG. 2B show 90° rotated cross sectional views of the embodiment of FIG. 1A and FIG. 1B, fitted with a retractable needle assembly. The arrows indicate that the plunger can be displaced in the distal direction, i.e., depressed.
Figure 2B:
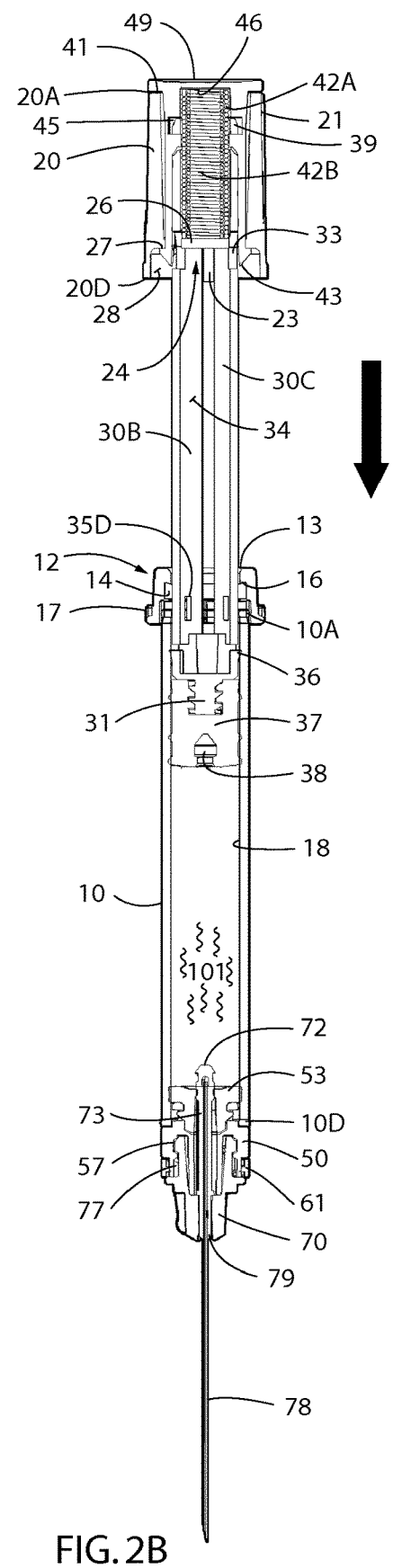

Additionally, as shown in FIG. 2A and FIG. 2B, proximal portion 61 remains attached to distal connector 50, even after the distal portion of cap 60 has been removed; providing visual feedback that the syringe may have been compromised if not used. In the embodiment of FIG. 1A and FIG. 1B, tip cap 60 is made of resilient plastic to facilitate the tamper-evident features, and thus stem 64 is a separate elastomeric, drug-compatible stem that is seated in and held in place within tip cap 60. Alternative mechanisms can be adapted for use with connectors in relation to tamper-resistant devices, and in certain embodiments may lack the biofeedback (tactile clues) associated with breaking tamper-resistant or tamper-evident seals.

Figure 8A:
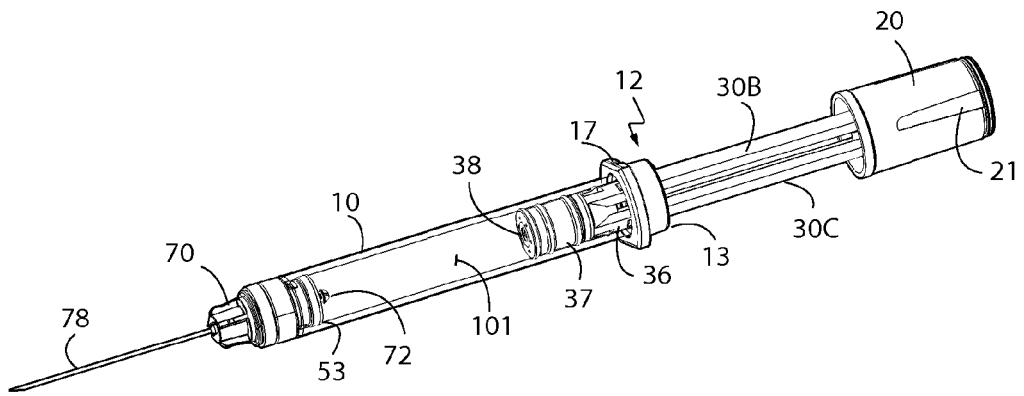
FIG. 8A and FIG. 8B depict two selectable retractable needle assemblies having needles of different length, each selected and attached to a retraction safety syringe fitted with an embodiment of a retraction plunger assembly.
Figure 8B:
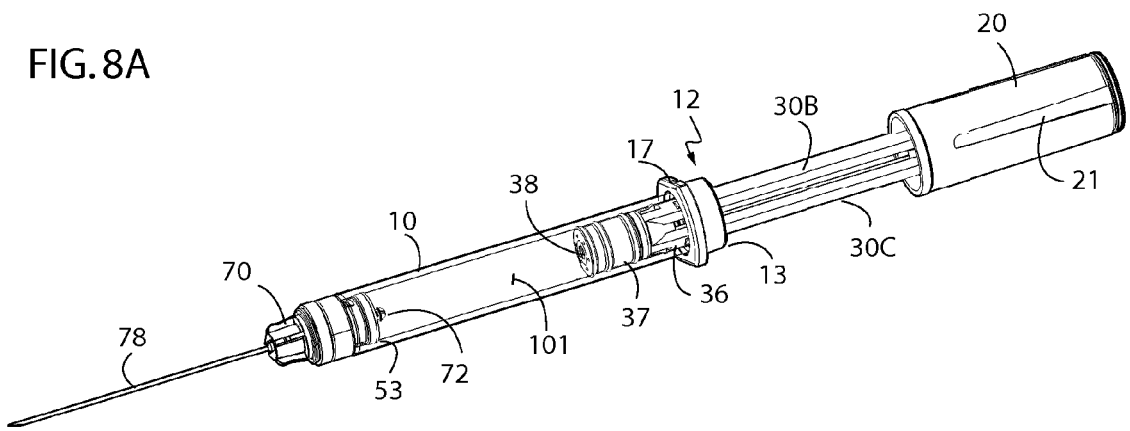

As shown in FIG. 2A and FIG. 2B, a selectable needle assembly can be selected and connected to the syringe to facilitate delivery of a substance via injection. The needle assembly can be any appropriate needle or needle assembly, without limitation, such as, for example, a retractable needle assembly. The design of the reaction plunger assembly allows for a wide selection of retractable needle assemblies, in which needles of desired length and gauge are available. See, e.g., FIG. 8A and FIG. 8B. In the embodiment of FIG. 2A and FIG. 2B, distal connector 50 houses a luer needle assembly having needle hub 70. Needle hub 70 includes screw threads 77 for connection to complementary screw threads 57 of distal connector 50. Needle 78 is contained in needle-over-mold 73, which is positioned in needle hub 70, needle 78 extending from the distal end 79 of needle-over-mold 73. In the embodiment of FIG. 2A and FIG. 2B, needle-over-mold 73 has proximal end 72, which end is configured with a protrusion to couple into recess 38 in plunger seal 37. The needle assembly can be configured such that screw threads 77 or other components thereof permanently secure the needle assembly to distal connector 50, as a further measure of tamper evidence or resistance. Note that in FIG. 2A and FIG. 2B, the proximal portion of tip cap 61 is engaged with connector 50, verifying that even if the needle is removed from connector 50, an operator would know that the syringe has been opened and should be considered "used." As noted, the distal connector may include additional elements or features that permanently engage the needle assembly with the syringe, however, such that single use and needle retraction are virtually unavoidable.

Further regarding FIG. 2A and FIG. 2B, once a retractable needle assembly has been selected and secured to the retraction syringe, the plunger may be displaced axially (i.e., pushed) into chamber space 101, in direction of the arrows (i.e., distally), to facilitate delivery of fluid contents of syringe (in this instance through needle 78). During depression, control unit 40 remains attached to housing 20, via detachable attachment 43 attached in housing bell 28 at ledge 27, and via retaining element 22 engaged with control unit 40 at receiving opening 48 and proximal plunger window 35A. As noted, chamber space 101 can be at least partially prefilled with contents to be delivered by the safety syringe. In this context, by "prefilled" is meant that the syringe as provided (e.g., by the manufacturer or distributor) to the operator (or pharmacist) has already been filled with deliverable fluid contents. Although this embodiment comprises needle 78, the retraction plunger assemblies described herein can be used with a broad range of needle assemblies, or needle-less access devices ("NLADs"), such as intravenous lines. Additionally, the retraction plunger assembly can be used with variety of different-length needles, as long as the needle assembly fits properly and includes an element that can couple with the distal end of the plunger for retraction. Additionally or alternatively, based on the basic design principles described herein, longer plunger assemblies can be provided for use with selectable needle assemblies having longer needle lengths (see, e.g., FIG. 8A and FIG. 8B).

Figure 3A:
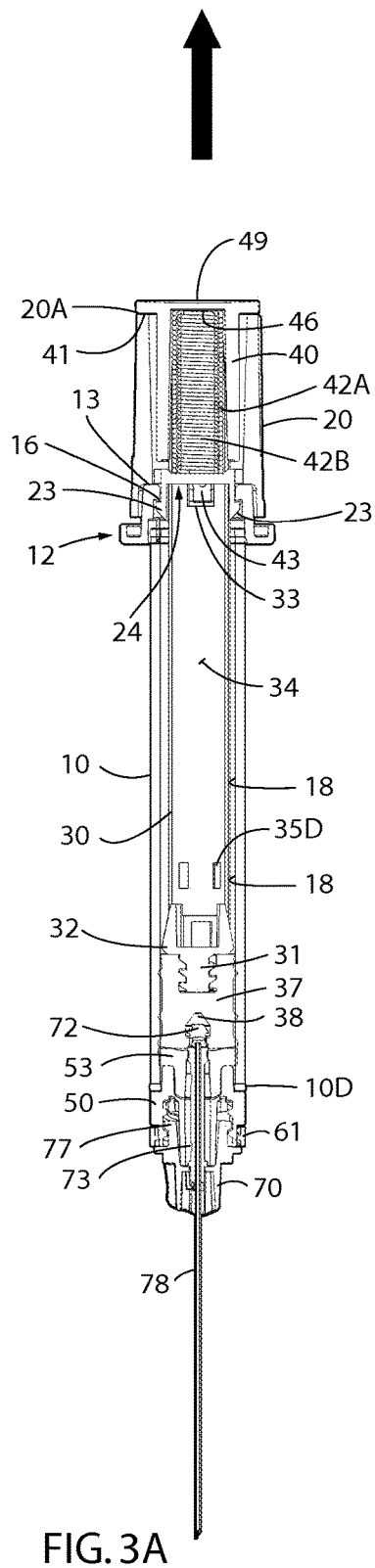
FIG. 3A and FIG. 3B show 90° rotated cross sectional views of the embodiment of FIG. 1A and FIG. 1B, at the end of delivery of the syringe contents. The arrows indicate the direction of control unit during the retraction process, i.e., upraised.
Figure 3B:
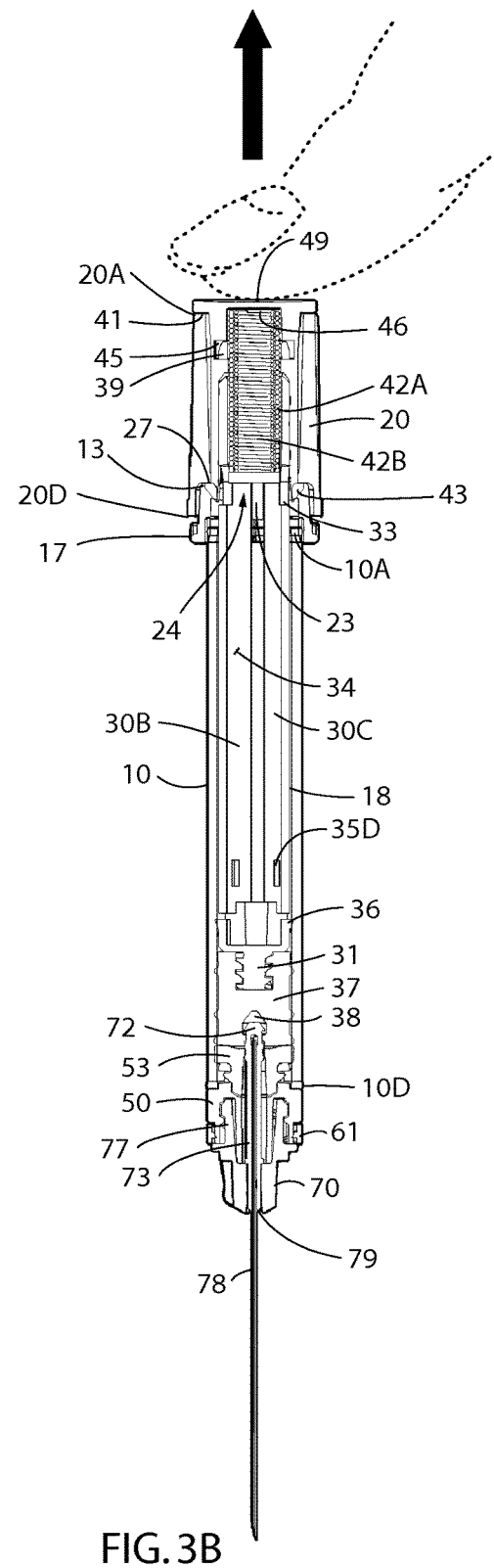

FIG. 3A and FIG. 3B illustrate this embodiment at the end of dose delivery. In this configuration, distal movement of plunger 30 has coupled recess 38 to proximal end protrusion 72 of the retractable needle assembly. Additionally, distal (downward) pressure placed on interface 49 causes detachable attachment 43 to press against release ring 13 of collar 12, which deforms attachment 43 inwardly toward opening 33 in plunger 30, thus detaching attachment 43 from housing interior ledge 27. The displacement of attachment 43 toward the interior of the control top and away from interior ledge 27 housing 20 is indicated by the arrows in FIG. 5C and FIG. 5D. The detachment of attachment 43 from ledge 27 also allows sufficient energy release from biasing members 42A and 42B to cause displacement of retainer element 22 from control unit opening 48 and plunger distal window 35D. The detachment of attachment 43 and displacement of retaining element 22 results in detachment and separation of control unit 40 from housing 20. This coincides with the movement of housing fastening 23 into interior 14 of collar 12, permanently securing fastening 23 and fitting 16 of collar 12. In this embodiment, fitting 16 is a ledge formed in the interior surface 14 of collar 12.

Thereafter, biasing members 42A and 42B release energy in opposing directions against surfaces 26 and 46, confined within the void space or cavity of plunger 34 and control unit 44, respectively. In this respect, plunger void 34 defines a retraction path for biasing members 42A and 42B. Additionally, at this juncture housing floor 26 is stationary in relation to syringe barrel 10 because housing 20 has been permanently secured to collar 12 via fastening 23 and ledge 16, such the control unit 40 (or proximal portions of a control rod) moves proximally past the interior surface 25 of housing 20; and plunger portions 30B and 30C are forced in the proximal direction through slots 24 by the energy released from biasing members 42A and 42B. As the "ceiling" of control unit 46 is pushed in the proximal direction while biasing members 42A and 42B extend through retraction path 34, the needle assembly coupled into the plunger (via coupling of protrusion 72 into recess 38), is translated in the proximal direction, which in turn translates needle-over-mold 73 and needle 78 into syringe barrel 10. Because an operator can maintain physical contact with interface 49, typically by maintaining position of the thumb or another digit on interface 49, as shown by the outlined digit in FIG. 3B, the operator can direct the upraising of control unit 40 and its associated features and elements, and thereby control the rate of retraction of needle 78 into barrel 10. Advantageously, by controlling the rate of needle retraction, the operator can reduce the likelihood of blood splattering, thereby improving the user-friendliness and appeal of the retraction syringe.

Figure 4A:
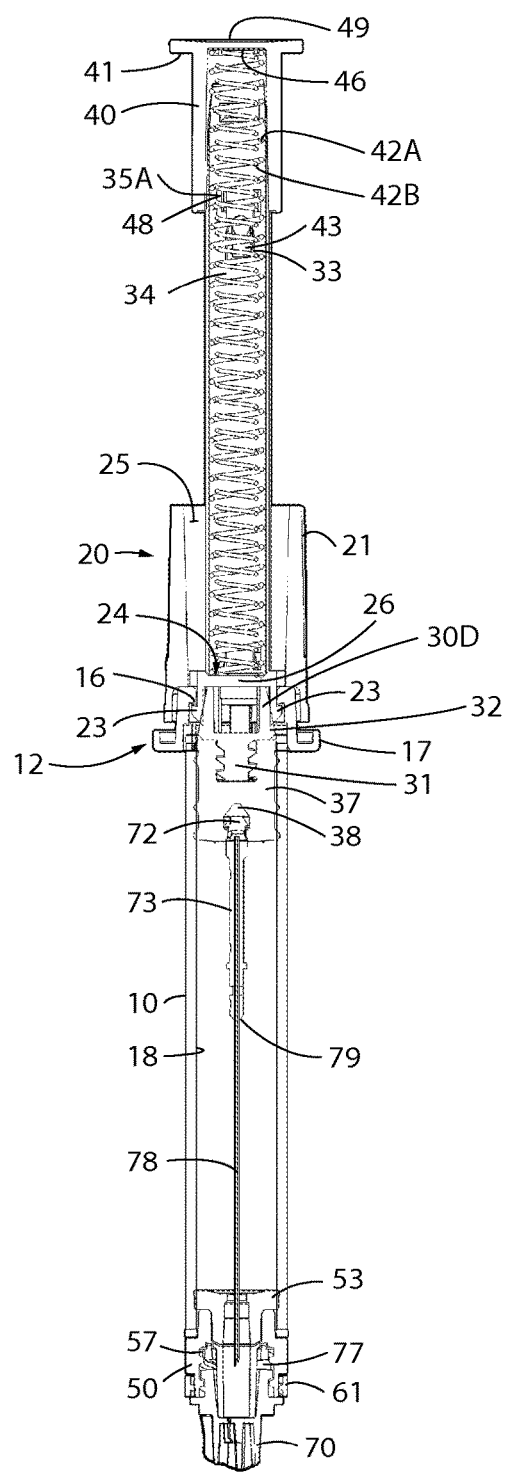
FIG. 4A and FIG. 4B show 90° rotated cross sectional views of the embodiment of FIG. 1A and FIG. 1B, following the conclusion of use, when the needle has been retracted into the syringe.
Figure 4B:
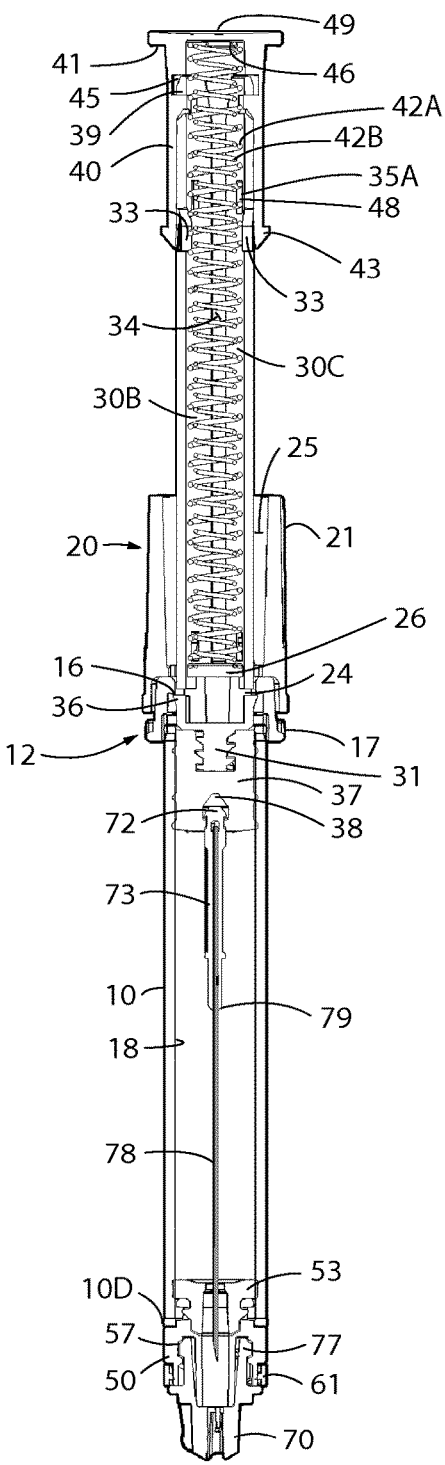
Figure 5A:
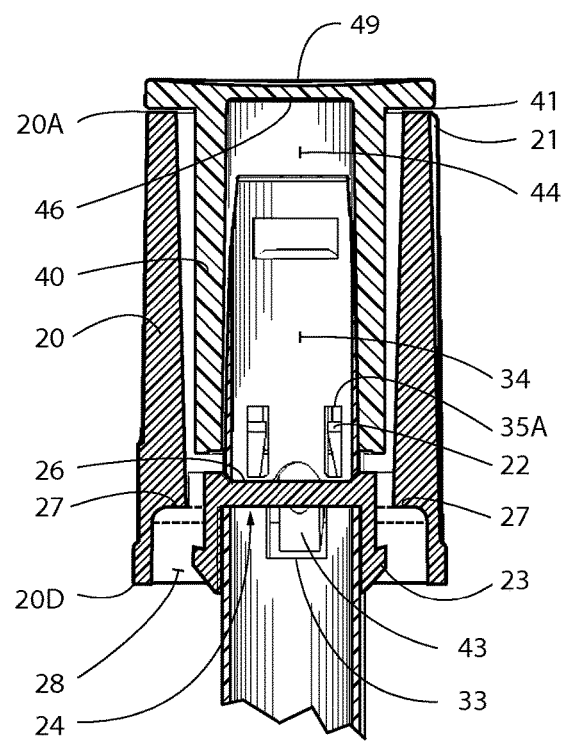
FIG. 5A-FIG. 5D show detailed views of the plunger assembly in an engaged position, excluding the biasing member(s), of an example embodiment.
Figure 5B:
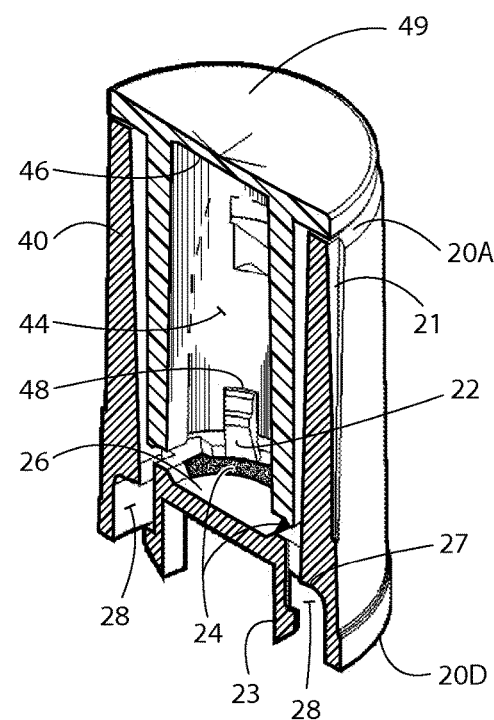
Figure 5C:
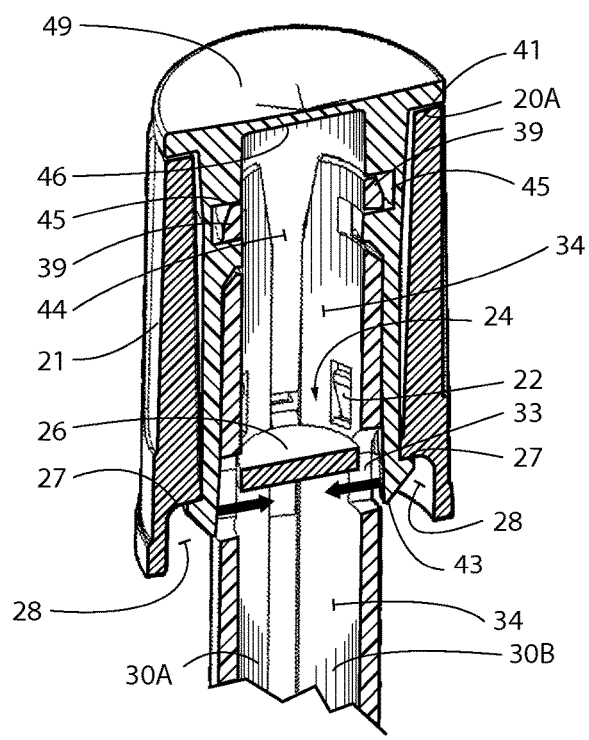
Figure 5D:
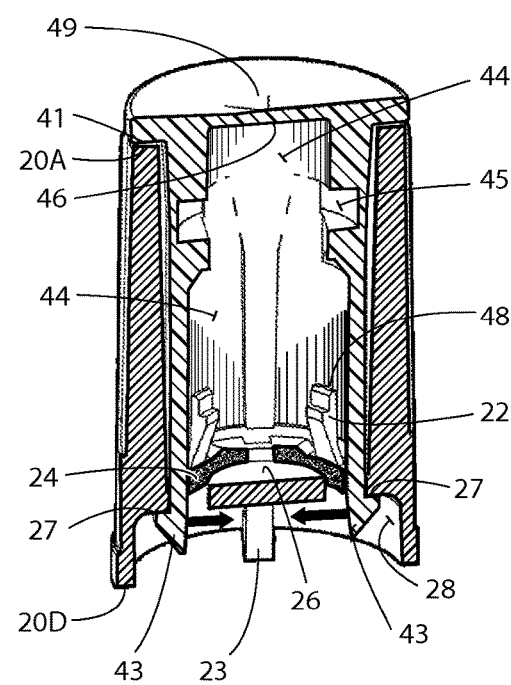

The fully retracted needle assembly of this embodiment is shown in FIG. 4A and FIG. 4B. Biasing members 42A and 42B rest in a de-energized state within void 34/44 of plunger/control rod. Housing 20 is secured in position at the proximal end of barrel 10 by fastening 23 and fitting 16. Control unit 40 is detached from housing 20, and at the fully proximal position. Needle 78 is enclosed in barrel 10. In addition to flared distal end sections 32 of plunger 30, externally flexed lock parts 36 prevent withdrawal of the plunger from syringe barrel 10, because plunger tabs 36 extend into interior 14 of collar 12 and abut ledge 16. Additionally, retainer element 22 is seated in distal window 35D of plunger 30, further locking movement of plunger 30 and its associated needle 78. Other locking means can be configured on the distal end of the plunger or proximal end of the barrel to further prevent removal of the plunger from the proximal end of the barrel or re-deployment of the needle. Additional locking means can be configured at the distal end of the distal connector of needle hub to further secure the needle or interior of the syringe.

At the position of the syringe components as shown in FIG. 4A and FIG. 4B, the operator may release contact with interface 49, although control unit 40, housing 20, or barrel 10, etc., can be handled without danger of needle sticks. Additionally, the device is configured such that the "lock-out" engagements, i.e., 22 with 35D, 23 with 16, and 36 with 16, are substantially covered by housing 20 and collar 12, and thus are not easily accessible or undone. Therefore, the plunger can neither be withdrawn from, nor pushed back into, the syringe without breaking the components and rendering the syringe incapable of being reused easily. These features minimize the risk of needle sticks from contaminated needles, and discourage users from sharing contaminated syringes.

Figure 6A:
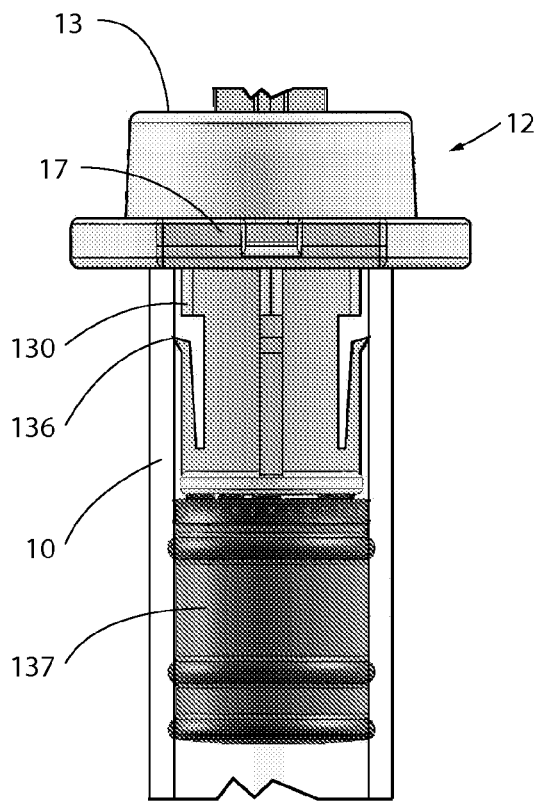
FIG. 6A-FIG. 6D show detailed views of plunger assemblies with different embodiments of locking parts, each configured to lock (or assist in locking) the plunger in a fixed position after the needle assembly has been retracted.
Figure 6B:
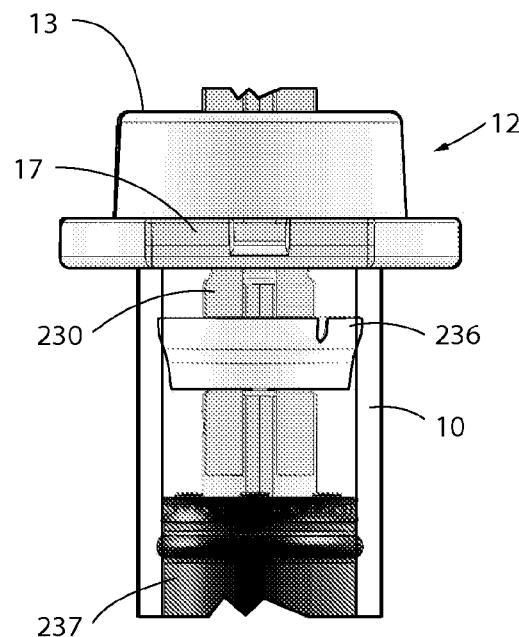

FIG. 6A-FIG. 6D show cross-sectional side views of various safety syringe components after retraction, comprising further embodiments of "lock-out" structures (lock parts) that may be used to prevent the plunger from being removed or re-engaged following retraction of the needle into the barrel. Some lock-out components may be used to prevent the plunger from being removed from the device, while other or the same lock-out components may be used prevent the plunger from being depressed in the distal direction. For example, in the embodiment of FIG. 6A, the distal end of plunger rod 130 includes outwardly flexed parts 136, which extend beyond the interior space 14 of collar 12 to prevent withdrawal of the plunger from syringe barrel 10. In the embodiment of FIG. 6B, plunger 230 includes a proximally facing flared disk that extends beyond the interior 14 of collar 12 to prevent withdrawal of the plunger from syringe barrel 10.

Figure 6C:
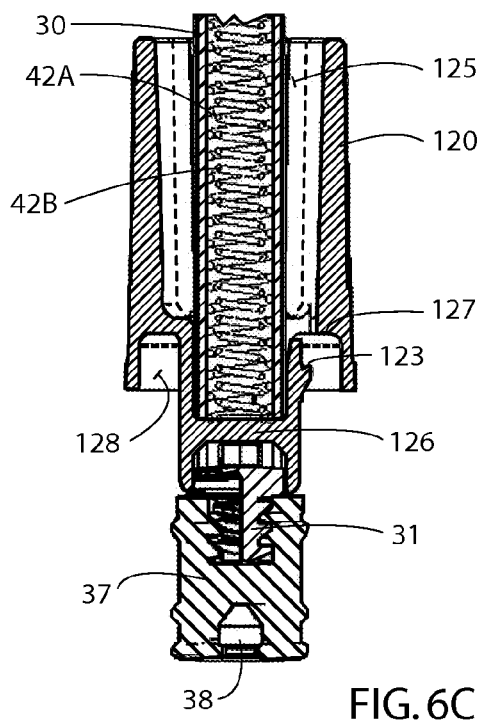

The embodiment of FIG. 6C includes a housing 120 that comprises fastening 123, which fastener engages irreversibly with fitting 16 such that the plunger cannot move after needle retraction. Advantageously, fastener 123 can also serve as a retaining element that engages with a corresponding proximal receiver in the plunger (e.g., window 35A of plunger 30) to stabilize the energized biasing member within the plunger assembly. See also FIG. 7.

Figure 6D:
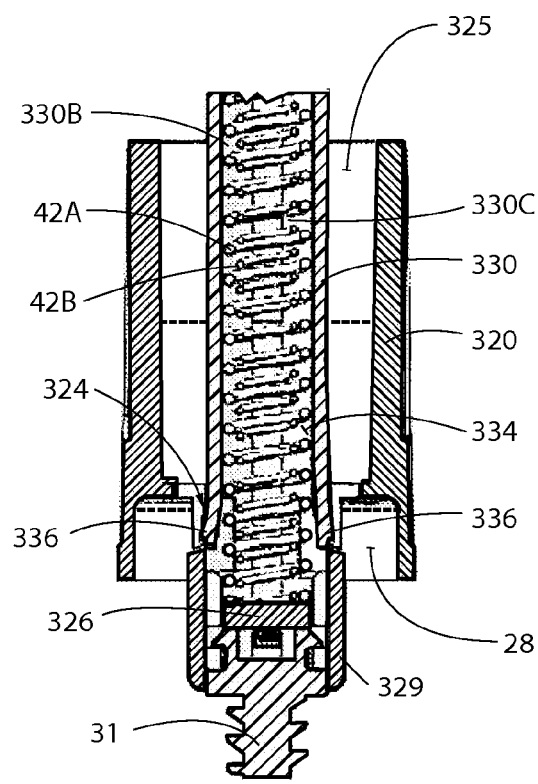

In the embodiment of FIG. 6D, plunger 330 and housing 320 are configured such that, following retraction of the needle, the distal portion of plunger 330 retracts into a channel formed by structure 329 of housing 320; and distal stops 336 of plunger 330 flair outwards and abut structure 329 above "floor" 326 of housing 320. In this configuration, stops 336 and 329 form a lock-out engagement that prevents distal movement of the plunger and its associated needle.

Figure 7:
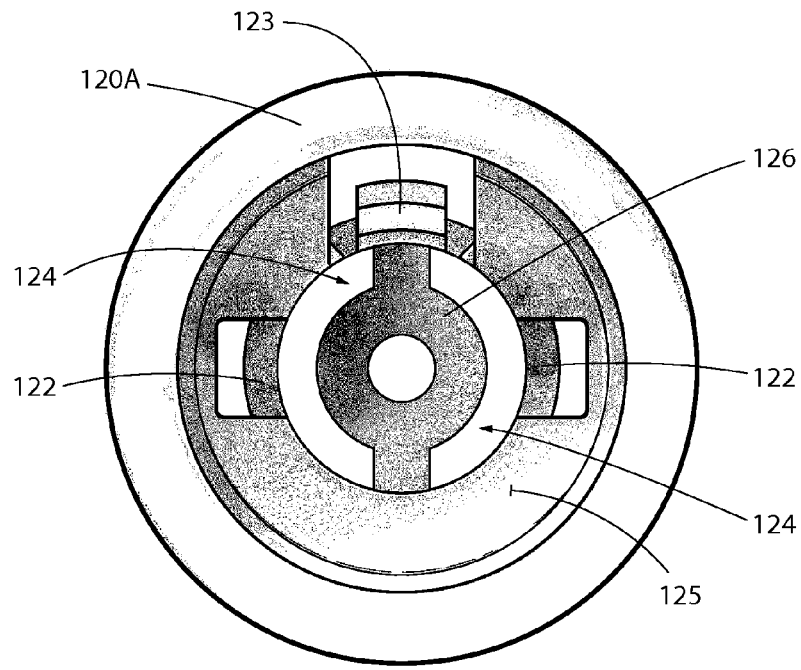
FIG. 7 shows a top-end view (looking from proximal surface through to the distal end) of an example of a housing component of an embodiment of a retraction plunger assembly.

FIG. 7 is a view from the top of an embodiment of housing 120 comprising retaining elements 122 and permanent fastener 123 (i.e., fastener 123 shown in FIG. 6C). Also visible are housing channel openings 124, through which plunger members 30B and 30C pass during needle retraction; and base "floor" 126 against which the distal end of the biasing means rests in the assembled device. Control unit 40 or an alternative control rod fit within opening 125 of housing 120 when the biasing member is compressed. Additionally, in this embodiment, base 126 is not a continuous solid piece but provides a suitable surface for positioning the distal end of a biasing member such as a spring (e.g., two springs 42A and 42B).

FIG. 8 illustrates the flexibility of the retraction plunger assemblies described herein, which provide for selection of a retractable needle assembly. More specifically, the present retraction plunger assemblies can be used with selectable retractable needle assemblies that have different needle lengths. Selection is limited only by the length of the barrel and coupled needle hub into which the needle must retract to protect the operator or patient from an inadvertent needle stick; as long as the plunger has sufficient length to engage with the retractable needle assembly.

Thus, as exemplified in the figures, the present embodiments may further utilize additional components to enhance the use of the syringe. For example, the retraction plunger assembly may incorporate tamper-resistance aspects to prevent tampering of the syringe. These tamper-resistance aspects deter or prevent a user from, for example, removing the plunger rod or providing evidence of tampering to the user. For example, these tamper-resistance aspects can be located along the housing, control unit, plunger, plunger seal, etc. These tamper-resistance aspects can be axially positioned or longitudinally oriented, or in a number of other known configurations. The tamper-resistance aspects may additionally or alternatively be located on an optional stability ring or flange of the plunger rod. In one embodiment, the tamper-resistance aspects may be tamper tabs. These tamper-resistance aspects impact upon or contact the barrel, collar, release ring, etc., to prevent pulling the plunger out of the barrel in the proximal direction or re-translating the plunger in the distal direction. Optionally, the syringes comprising the retraction plunger assemblies of the present embodiments may utilize tamper-evident features. For example, the syringes or distal connectors may utilize an over-sized or specially-shaped tip cap that cannot be reinserted into the syringe after removal. Alternatively, syringes or connectors may utilize tamper tabs that connect the tip cap to itself through a window in the connector during assembly, but cannot be reassembled. As a further embodiment, the tip cap or tip cap assembly may be bonded to the barrel tip during assembly, and a broken bond could be utilized to provide visual indication of tampering.

A further aspect of these embodiments provides for kits comprising retraction safety syringes or components thereof, such as retraction assemblies. In one example embodiment, a kit can include (a) a syringe comprising a prefilled barrel fitted with a retraction plunger assembly, as described herein, and a distal connector connected to a tip cap, and (b) a selection of retractable needle assembles. The retractable needle assemblies may provide needles of different lengths or different gauge, such that, for example, a healthcare professional can select the needle best suited for delivering the syringe contents to a particular patient.

In another example embodiment, the retraction syringe kit can include a vial adapter. For example, the vial adapter can include a housing having a base, an adapter cannula that extends or projects from the base, and a connector configured for fluid communication with fluid contents of the vial and the barrel of the retraction syringe; the adapter housing further comprising a shroud to protect a user from inadvertent needle-stick from the adapter cannula, the shroud comprising one or more arms that engage a vial closure. The shroud may further comprise one or more flexion arms that allow the vial adapter to engage any of a variety of different-sized vial closures. In use, the vial adapter facilitates transfer or delivery of fluid between the vial and the retraction syringe barrel, to thereby allow fluid reconstitution of a solid substance contained within the syringe barrel or within the vial. The vial adapter may further comprise a conduit tip, mountable or mounted to the connector to provide fluid communication with the adapter cannula, which conduit tip prevents inadvertent activation of the syringe retraction mechanism during fluid transfer.

In a further aspect, the embodiments described herein provide for a method of assembling a safety syringe, including the step of mounting a retractable needle assembly to a barrel of a syringe fitted with a retraction plunger assembly. For example, the method includes the step of removing a tip cap from the distal connector of the barrel prior to mounting the retractable needle assembly to the barrel. methods of using a retraction safety syringe, comprising the steps of, for example, obtaining a retraction safety syringe comprising the retraction plunger assembly as described herein, wherein the syringe is fillable or prefilled with a substance; selecting a retractable needle assembly having a retractable needle portion configured to couple to the plunger; and attaching the selected retractable needle assembly to the retraction safety syringe. Additionally, the method can include depressing the control unit to expel the substance and couple the plunger to the retractable needle portion, secure the permanent fastener of the housing to a fitting disposed at the proximal end of the syringe barrel, and detach the control unit from the housing, thereby releasing the biasing member from the energized state; and upraising or retracting the control unit at a controlled rate to retract the needle into the syringe.

Each of the embodiments described herein may be used alone or in combination with one or more other embodiments in a syringe. Various changes and modifications may be made to the embodiments described and illustrated. Throughout the specification, the aim has been to describe example embodiments without limiting the claimed invention to any one embodiment or specific collection of features.

We claim:

1. A retraction plunger assembly for use with a safety syringe comprising:
   a plunger configured for positioning and axial displacement within a syringe barrel, the plunger having a proximal portion, a distal portion, and a cavity there between, wherein the distal portion of the plunger is fixed to a plunger seal that includes a coupling configured to couple to a retractable needle portion of a retractable needle assembly;
   a control unit fixed at the proximal portion of the plunger, wherein the control unit comprises at least one detachable attachment for detachably attaching to a housing;
   a housing detachably attached to the control unit, wherein the housing comprises at least one permanent fastening configured to secure the housing to a fitting disposed at the proximal end of the syringe barrel; and
   at least one biasing member disposed in an energized state within the plunger assembly, wherein the biasing member is initially positioned between the control unit and housing and at least partially within the plunger cavity, and wherein the control unit attachment to the housing maintains the biasing member in the energized state.

2. The retraction plunger assembly of claim 1, wherein the housing further comprises at least one retaining element configured to reversibly link at least one of the control unit, the plunger, or a biasing member.

3. The retraction plunger assembly of claim 1, further comprising at least one locking part configured to lock the plunger in a fixed position.

4. A safety syringe comprising:
   a barrel having a proximal end and a distal end;
   the distal end of the barrel comprising a distal connector configured to engage a retractable needle assembly;
   a retraction plunger assembly comprising
      a plunger disposed in the proximal end of the barrel and configured for axial displacement within the barrel, the plunger having a proximal portion, a distal portion, and a cavity there between,
      a control unit fixed at the proximal portion of the plunger,
      a housing detachably attached to the control unit, and
      at least one biasing member disposed within the plunger assembly, wherein the biasing member is initially positioned between the control unit and housing and at least partially within the plunger cavity; and
   a release member disposed at the proximal end of the barrel and configured to detach the housing from the control unit upon full depression of the plunger into the barrel.

5. The syringe of claim 4, wherein the control unit comprises at least one detachable attachment for detachably attaching to the housing.

6. The syringe of claim 5, wherein the housing comprises at least one permanent fastener configured to secure the housing to a fitting disposed at the proximal end of the barrel.

7. The syringe of claim 4, wherein the release member further comprises a fitting to permanently secure the housing.

8. The syringe of claim 7, wherein the release member and fitting are included in a collar affixed to the proximal end of the syringe barrel.

9. The syringe of claim 4, wherein the housing comprises at least one retaining member configured to reversibly link at least one of the control unit, the plunger, or the biasing member.

10. The syringe of claim 9, wherein the retaining member is further configured to permanently secure the housing to a fitting disposed at the proximal end of the barrel.

11. The syringe of claim 4, wherein the distal portion of the plunger further comprises a plunger seal.

12. The syringe of claim 11, wherein the plunger seal further comprises a coupling configured to couple to a retractable needle portion of a retractable needle assembly.

13. The syringe of claim 4, wherein the distal portion of the plunger further comprises a coupling configured to couple to a retractable needle portion of a retractable needle assembly.

14. The syringe of claim 4, wherein the biasing member is held in an energized state when the control unit is attached to the housing.

15. The syringe of claim 13, wherein upon full depression of the plunger into the barrel, the release member detaches the control unit from the housing, allowing the biasing member to transform from an energized to a non-energized state.

16. The syringe of claim 4, wherein the biasing member is no longer held in an energized state when the control unit is detached from the housing.

17. The syringe of claim 4, further comprising at least one locking part configured to lock the plunger in a fixed position following needle retraction.

18. The syringe of claim 4, further comprising at least one locking part that locks the plunger in a fixed position following retraction.

19. A safety syringe comprising:
a barrel having a proximal end and a distal end;
the distal end of the barrel comprising a distal connector configured to engage a retractable needle assembly;
a retraction plunger assembly comprising
a plunger disposed in the proximal end of the barrel and configured for axial displacement within the barrel, the plunger having a proximal portion, a distal portion, and a cavity there between, wherein the distal portion of the plunger is fixed to a plunger seal including a coupling configured to couple to a retractable needle portion of a retractable needle assembly
a control unit fixed at the proximal portion of the plunger, wherein the control unit comprises at least one detachable attachment for detachably attaching to a housing,
a housing detachably attached to the control unit, wherein the housing comprises at least one permanent fastener configured to secure the housing to a fitting disposed at the proximal end of the barrel, and at least one retaining member configured to reversibly link at least one of control unit, plunger, or biasing member,
at least one biasing member disposed in an energized state within the plunger assembly, wherein the biasing member is initially positioned between the control unit and housing and at least partially within the plunger cavity; and
a collar affixed to the proximal end of the syringe barrel, the collar comprising a release member configured to detach the housing from the control unit upon full depression of the plunger into the barrel, and a fitting to permanently secure the housing to the proximal end of the barrel.

20. The syringe of claim 19, wherein upon full depression of the plunger into the barrel, the permanent fastener of the housing secures the housing to the collar fitting and the release member detaches the control unit from the housing, releasing the biasing member from the energized state and thereby retracting the plunger from the fully depressed position to a retracted position; wherein the rate of retraction is controlled by upraising the control unit.

21. The syringe of claim 19, wherein the retaining member of the housing is further configured to lock the housing to a fitting disposed at the proximal end of the barrel.

22. A kit comprising the retraction plunger assembly of claim 4.

23. The kit of claim 22, further comprising at least one retractable needle assembly having a retractable needle portion configured to couple to the plunger.

24. A method of using a retraction safety syringe, comprising:
obtaining a retraction safety syringe comprising the retraction plunger assembly of claim 4, wherein the syringe is fillable or prefilled with a substance;
selecting a retractable needle assembly having a retractable needle portion configured to couple to the plunger; and
attaching the selected retractable needle assembly to the retraction safety syringe.

25. The method of claim 24, further comprising:
depressing the control unit to expel a substance and couple the plunger to the retractable needle portion, secure the permanent fastening of the housing to a fitting disposed at the proximal end of the syringe barrel, and detach the control unit from the housing, thereby releasing the biasing member from the energized state; and
upraising the control unit at a controlled rate to retract the needle into the syringe.

* * * * *